United States Patent
Harima et al.

(10) Patent No.: US 8,349,357 B1
(45) Date of Patent: Jan. 8, 2013

(54) ADHESIVE PATCH AND ADHESIVE PREPARATION

(75) Inventors: Jun Harima, Ibaraki (JP); Masakatsu Konno, Ibaraki (JP); Ryo Hashino, Ibaraki (JP); Akira Numata, Ibaraki (JP)

(73) Assignee: Nitto Denko Corporation, Ibaraki-shi, Osaka (JP)

( * ) Notice: Subject to any disclaimer, the term of this patent is extended or adjusted under 35 U.S.C. 154(b) by 0 days.

(21) Appl. No.: 13/224,075

(22) Filed: Sep. 1, 2011

(51) Int. Cl.
*A61L 15/16* (2006.01)

(52) U.S. Cl. ........................................ 424/447; 424/449

(58) Field of Classification Search .................... None
See application file for complete search history.

(56) References Cited

FOREIGN PATENT DOCUMENTS

| EP | 0 264 299 A2 | 10/1987 |
| EP | 2 158 884 A2 | 3/2010 |
| JP | 06-063071 A | 3/1994 |
| JP | 11-001432 A | 1/1999 |

OTHER PUBLICATIONS

European Patent Office, European Search Report in European Patent Application No. 11 17 9763 (Jan. 26, 2012).

*Primary Examiner* — Bethany Barham
(74) *Attorney, Agent, or Firm* — Leydig, Voit & Mayer, Ltd.

(57) ABSTRACT

The present invention provides an adhesive patch comprising a support, an adhesive layer on at least one surface of the support, and a release liner on a surface of the adhesive layer opposite from the support, wherein
(a) the lateral end of the adhesive layer is exposed,
(b) in at least one lateral end, the lateral end of the adhesive layer is located toward the central part side of the adhesive patch from the lateral end of the support, and
(c) when placed horizontally with the release liner facing down, a distance A between the upper end of the support and the lower end of the release liner at said lateral end of the adhesive patch is greater than a thickness B of the central part of the adhesive patch.

16 Claims, 6 Drawing Sheets

500 μm/div

500 μm/div

500 μm/div

500 μm/div

ADHESIVE PATCH AND ADHESIVE PREPARATION

TECHNICAL FIELD OF THE INVENTION

The present invention relates to an adhesive patch comprising a support and an adhesive layer formed on at least one surface of the support, and an adhesive preparation.

BACKGROUND OF THE INVENTION

In recent years, various adhesive patches and adhesive preparations have been developed. Adhesive preparation and adhesive preparation are highly superior in terms of protection of wound surface, continuous transdermal administration of a drug, drug metabolism by first-pass through the liver, and avoidance of various side effects.

In general, adhesive patches and adhesive preparations have a support made of a woven fabric, a non-woven fabric, a plastic film and the like and an adhesive layer laminated on the support, and are generally provided with a release liner laminated on the adhesive layer. They are provided in a package made of a packaging material such as a resin film and the like.

In such adhesive patches and adhesive preparations, the adhesive layer is required to have a certain thickness in consideration of the wound surface protection effect, and the effective drug content. However, when the adhesive layer becomes thick, the end of the adhesive patch and the like is easily rubbed against clothes and the like and turned up, as well as the components of the adhesive layer ooze or protrude from the end of the adhesive patch and the like, i.e., cold flow, thus posing problems during adhesion to the skin.

Cold flow occurs depending on the property of the adhesive layer. It often occurs when, in particular, an adhesive patch or adhesive preparation is under a load for a long time, that is, when an adhesive patch and the like are contained in a package and stored for a long period and the like.

Adverse effects of cold flow include, for example, difficulty in taking out an adhesive patch and the like from a package, which is caused by adhesion of oozed or protruded adhesive layer components to the inside of the package, turning and staining of adhesive patch and the like during adhesion to the skin, a lower medicinal effect of the adhesive preparation due to an outflow of the drug and the like. Therefore, adhesive patches and adhesive preparations desirably have an end not easily rubbed against clothes, do not permit easy cold flow, and have an adhesive layer retaining the original shape.

As a technique to handle such problem, JP-A-11-1432 (patent document 1) discloses an adhesive patch having a dry edge, which has a release liner extended from the end of a support and an adhesive layer. In such adhesive patch, oozing and protruding of an adhesive layer component from the end of an adhesive layer in contact with a release liner can be suppressed to some extent. However, in such adhesive patch, oozing and protruding of an adhesive layer component from the end of an adhesive layer in contact with a support may occur, and the preparation is not entirely satisfactory.

JP-A-6-63071 (patent document 2) discloses a covering material for wound (dressing material) which is contoured and has an adhesive layer fitting to the skin. In one example of this covering material for wound, the end is cut flatly, and therefore, oozing and protruding of an adhesive layer component from the end may occur, which results in the attachment of the component to the inner surface of the package.

In another example described in patent document 2, the end of the covering material is covered with a support. In such adhesive patch, however, the end of a support covers the end of an adhesive layer and, at the end of the adhesive patch, the end of the support aligns with the end of the release liner. Therefore, when in use, the release liner may not be easily detached from the end thereof with fingers. In addition, since the end of the support needs to be able to bend and cover the end of an adhesive layer, the degree of freedom of selection of the material and shape thereof, particularly thickness and the like, is low. Particularly, when the adhesive layer is thick, it is not easy to cover the end of the adhesive layer with the end of the support extended therefor in an industrial production stage. In fact, the thickness of the end of the adhesive layer of the adhesive patch in this example is molded to be thinner than that of the central part, and the thickness of the end of the adhesive layer is inferred to be difficult to maintain.

DOCUMENT LIST

Patent Documents patent document 1: JP-A-11-1432
patent document 2: JP-A-6-63071

SUMMARY OF THE INVENTION

Problems to be Solved by the Invention

Thus, the development of an adhesive patch and an adhesive preparation, which satisfy (i) easiness in taking out from package, (ii) releaseability of a release liner from an adhesive layer during use, and (iii) high adhesion performance to the skin is desired.

The present invention has been made in view of such situation, and the problem to be solved is to provide an adhesive patch or an adhesive preparation, which is characterized in that
(i) oozing or protruding of an adhesive layer component from the end of an adhesive patch and the like is suppressed, attachment of the adhesive patch and the like to the inner surface of a package is suppressed during preservation in the package, and the preparation can be taken out easily from the package;
(ii) the frequency of rubbing of the end against clothes etc. is reduced during adhesion to the skin, the end is not turned up easily, sufficient skin adhesion is ensured, and the preparation is highly resistant to the detachment from the skin surface; and
(iii) during use, the release liner can be easily detached from the adhesive layer.

Means of Solving the Problems

The present inventors have conducted intensive studies in an attempt to solve the above-mentioned problems, and found that the aforementioned problems can be achieved when, in at least one lateral end of an adhesive patch and the like, the lateral end of an adhesive layer is located toward the central part side of the adhesive patch and the like from the lateral end of the support, and the distance between the upper end of the support and the lower end of the release liner of the adhesive patch and the like at said end part is greater than the thickness of the adhesive patch and the like in the central part, which resulted in the completion of the present invention.

Accordingly, the present invention relates to the following [1] to [9].

[1] An adhesive patch comprising a support, an adhesive layer on at least one surface of the support, and a release liner on a surface of the adhesive layer opposite from the support, wherein
(a) the lateral end of the adhesive layer is exposed,
(b) in at least one lateral end, the lateral end of the adhesive layer is located toward the central part side of the adhesive patch from the lateral end of the support, and
(c) when placed horizontally with the release liner facing down, a distance A between the upper end of the support and the lower end of the release liner at said lateral end of the adhesive patch is greater than a thickness B of the central part of the adhesive patch.

[2] The adhesive patch of the above-mentioned [1], wherein, in at least one lateral end, the lateral end of the adhesive layer is located on the central part side of the adhesive patch at 1 μm-1000 μm from the lateral end of the support.

[3] The adhesive patch of the above-mentioned [1], wherein, in at least one lateral end, the distance A between the upper end of the support and the lower end of the release liner at said lateral end of the adhesive patch is greater than a thickness C of the adhesive patch at the lateral end of the adhesive layer.

[4] The adhesive patch of the above-mentioned [1], wherein, in at least one lateral end, the thickness C of the adhesive patch at the lateral end of the adhesive layer is equal to the thickness B of the central part of the adhesive patch.

[5] The adhesive patch of the above-mentioned [1], wherein, in at least one lateral end, the end of the adhesive layer has a concave shape.

[6] The adhesive patch of any of the above-mentioned [1] to [5], wherein the adhesive layer comprises a rubber-based adhesive.

[7] The adhesive patch of any of the above-mentioned [1] to [6], wherein the adhesive layer is not crosslinked.

[8] The adhesive patch of any of the above-mentioned [1] to [7], wherein the adhesive layer comprises an organic liquid component.

[9] An adhesive preparation comprising the adhesive patch of any of the above-mentioned [1] to [8], wherein the adhesive layer contains a drug.

Effect of the Invention

In the adhesive patch or adhesive preparation of the present invention, in at least one lateral end, the lateral end of the adhesive layer is located toward the central part side of the adhesive patch and the like from the lateral end of the support. Therefore, oozing or protruding of an adhesive layer component from the end of the adhesive patch or adhesive preparation does not occur easily and the cold flow phenomenon is suppressed during the preservation of the adhesive patch or adhesive preparation. As a result, attachment of the adhesive patch and the like to the inner surface of the package is suppressed, and the adhesive patch and the like can be easily taken out from the package. In addition, stickiness to hand and sticky feeling at the applied site, which cause an unpleasant feeling, occur less often when in use.

Moreover, in the adhesive patch and adhesive preparation of the present invention, the lateral end of the adhesive layer is exposed and is not covered with a support or a release liner. This combined with the aforementioned improved easiness in taking out the adhesive patch and the like from a package, which is attributable to the suppression of oozing and protrusion of an adhesive layer component, the adhesive patch and the like of the present invention permits easy detachment of the release liner from the end thereof with fingers when in use.

Still more difficult to predict, an adhesive patch and the like wherein, in at least one lateral end, distance A between a support upper end and a release liner lower end is greater than distance B of the central part of the adhesive patch and the like, do not drop off easily for a long time when applied to the skin.

DESCRIPTION OF EMBODIMENTS

In the present specification, an "adhesive patch" is a concept encompassing not only preparations aiming at transdermal absorption of a drug but also a material for medical care or hygiene of skin such as a skin protection sheet and the like, which does not contain an active ingredient such as a drug and the like. One containing a drug is to be particularly referred to as a "adhesive preparation".

As a material for medical care or skin hygiene of the adhesive patches of the present invention, adhesive plaster, tape for skin, dressing material for covering wound and the like can be mentioned. They are provided in the form of film, sheet, pad and the like. The adhesive preparation can also be provided as a transdermal absorption type preparation aiming at a local or systemic action, which is of either a matrix type or a reservoir type. The dosage form may vary and may be a patch type, an adhesive tape type, a sheet type and the like. When simply referred to as an "adhesive patch" in the following, the term also encompasses an adhesive preparation. In addition, a laminate of an adhesive layer and a support is to be referred to as an "adhesive patch main part".

Now the present invention is explained in the following by referring to the attached drawings. In FIG. 1-FIG. 5, each element is schematically shown, and therefore, the ratios of the size and the like of elements are different from those of actual adhesive patch and the like.

The adhesive patch of the present invention has a substantially flat planar shape. The flat shape of the adhesive patch of the present invention includes, but is not limited to, for example, about rectangle, polygon such as triangle, pentagon and the like, or a shape defined by about straight lines, a shape defined by curved lines such as ellipse, circular shape and the like, a combination thereof and the like. The size of the adhesive patch is not limited, and can be selected as appropriate according to the use, application site and the like of the adhesive patch. For example, when the adhesive patch has an about rectangular shape, the length of one side thereof is generally 15 mm-90 mm, and the length of the other side is generally 15 mm-90 mm. In the present specification, when plural distinguishable areas are present in the flat plane of the adhesive patch of the present invention, an area containing the center of gravity of the flat plane of the adhesive patch is referred to as a central part, and an area containing the contoured part of the flat plane of the adhesive patch, which is present outside the aforementioned central part, is referred to as a peripheral part. In addition, the thickness of the adhesive patch central part is the thickness of the core part of the adhesive patch, namely, at the gravity center of the flat plane of the adhesive patch.

Figure 1:
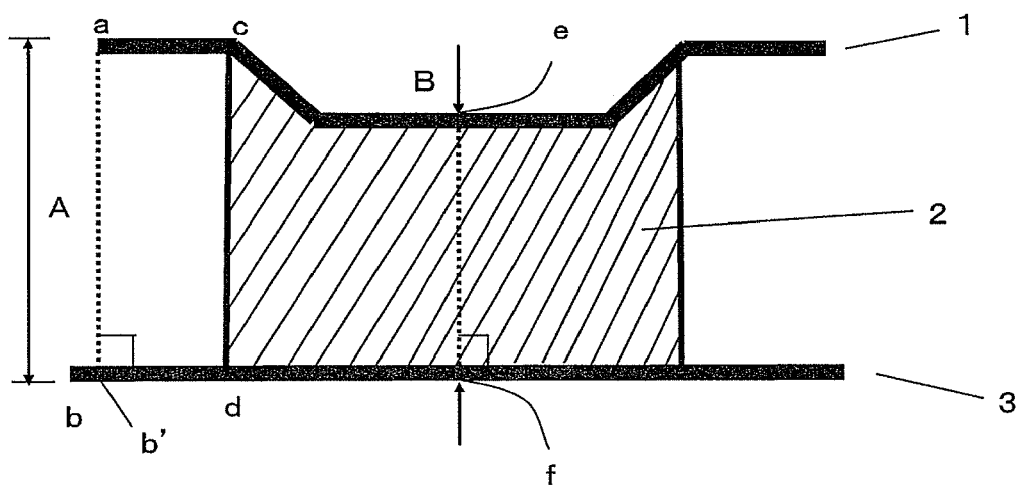
FIG. 1 is a schematic sectional view of one embodiment of the adhesive patch or adhesive preparation of the present invention.

The adhesive patch of the present invention has an adhesive layer on at least one surface of a support and a release liner on the opposite surface of the adhesive layer. The lateral end of the adhesive layer is exposed and, in at least one lateral end of the adhesive patch, the lateral end of the adhesive layer is located toward the central part side of the adhesive patch from the lateral end of the support. That is, in FIG. 1 schematically showing the cross section of the adhesive patch of the present invention, a line segment cd binding an upper end c of the support 1 and a lower end d of a release liner 3 at the lateral end of an adhesive layer 2 is located toward the central part side of the adhesive patch from a line segment ab binding an upper end a of the support 1 and a lower end b of the release liner 3. Such shape can be formed by contouring the adhesive layer as mentioned above during formation of an adhesive layer on a support or a release liner. For example, an adhesive layer is formed such that the contoured part of the adhesive layer is located toward the central part side of an adhesive patch from a part corresponding to the contoured part of a support of the adhesive patch. Alternatively, in an adhesive patch wherein the lateral ends of a support and an adhesive layer are on the same flat plane, the aforementioned shape is formed by breaking away one part of the lateral end of the adhesive layer. In the present specification, the cross section shown in each drawing is that of an adhesive patch cut in the perpendicular direction from the surface of support 1.

In the adhesive patch of the present invention, moreover, when the adhesive patch is placed on the horizontal plane with a release liner facing downward, distance A between the upper end of a support and the lower end of a release liner at the above-mentioned lateral end of the adhesive patch, namely, the length of the perpendicular line ab' drawn from an upper end a of support 1 to the lower end of release liner 3 in FIG. 1 is greater than the length of thickness B in the adhesive patch central part, i.e., a perpendicular line of drawn from the upper end e of the support 1 to the lower end of release liner 3 in the adhesive patch core part in FIG. 1. In the present invention, A is preferably 101%-200%, more preferably 101%-150%, of B. Being difficult to predict, when an adhesive patch having the aforementioned constitution is applied to the skin, it does not drop off easily for a long time. When a part free of an adhesive layer is formed in an end part of the adhesive patch, the skin adhesive force at the end of the adhesive patch generally decreases and the adhesive patch is expected to drop off from the skin with ease. According to the present invention having the aforementioned shape, however, when an adhesive patch is applied to the skin, the lateral end of the support pushes up the clothes somewhat and keeps the clothes off from the lateral end. Thus, the adhesive patch main part does not drop off from the skin for a long time. As a method for achieving such shape, a method including laminating a support preliminarily molded in the aforementioned shape on an adhesive layer, and a method including laminating a tabular support on an adhesive layer, and molding the adhesive patch in the aforementioned shape can be used.

In a preferable embodiment of the present invention, in at least one lateral end of the adhesive patch, the lateral end of the adhesive layer is located at 1 μm-1000 μm, more preferably 100 μm-800 μm, toward the central part side of the adhesive patch from the lateral end of the support. That is, in FIG. 1, the length of a line segment ac connecting an upper end a of the support 1 and an upper end c of the support 1 in the lateral end of an adhesive layer 2 is 1 μm-1000 μm, more preferably 100 μm-800 μm. When the lateral end of the adhesive layer 2 is located at 1 μm-1000 μm from the lateral end of the support 1, oozing or protruding of an adhesive layer component from the lateral end of the adhesive patch can be sufficiently suppressed during the preservation of the adhesive patch, and the adhesive force at the lateral end of the adhesive patch does not decrease often.

Figure 2:
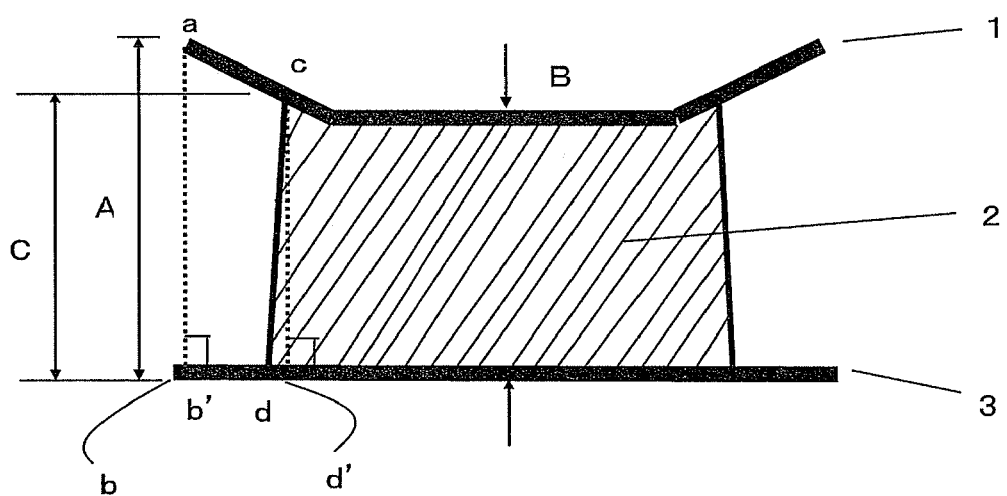
FIG. 2 is a schematic sectional view of one embodiment of the adhesive patch or adhesive preparation of the present invention.

Moreover, in another preferable embodiment of the present invention, when an adhesive patch is placed on a horizontal plane with a release liner facing down, in at least one lateral end of the adhesive patch, distance A between the support upper end and the release liner lower end at the lateral end is greater than thickness C of the adhesive patch at the lateral end of the adhesive layer. That is, in FIG. 2 showing a schematic sectional view of the adhesive patch of the embodiment, the length of a perpendicular line ab' drawn from an upper end a of support 1 to the lower end of release liner 3 at the lateral end of the adhesive patch is greater than perpendicular line cd' drawn from upper end c of the support 1 to the lower end of release liner 3, in the lateral end of the adhesive layer 2. In the present invention, A is preferably 101%-200%, more preferably 101%-150%, of C. In the adhesive patch of this embodiment, C is greater than B.

Depending on the production method and molding method of the adhesive patch, moreover, an adhesive patch may contain a peripheral part and a central part thicker than the peripheral part. In this case, even when thickness C of the adhesive patch at the lateral end of the adhesive layer is thinner than thickness B of the adhesive patch central part in, when distance A between the support upper end and the release liner lower end at the lateral end is greater than thickness B of the adhesive patch at the central part of the adhesive layer, by placing an adhesive patch on a horizontal plane with a release liner facing down, the adhesive patch is encompassed in the adhesive patch of the present invention.

Figure 3:
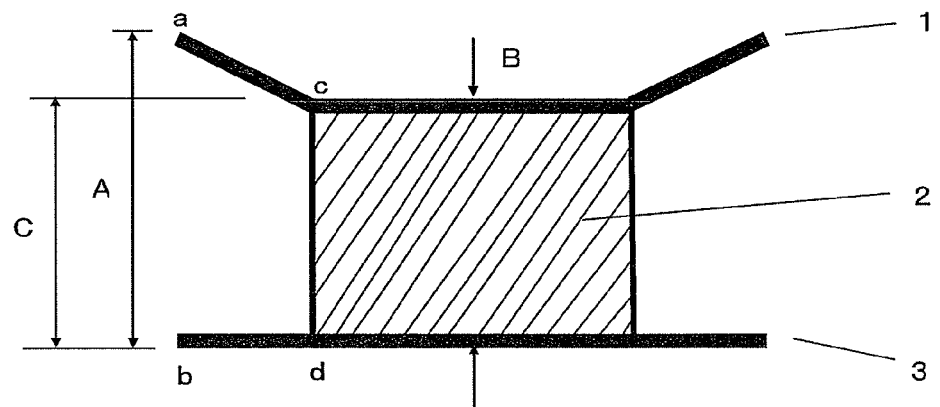
FIG. 3 is a schematic sectional view of one embodiment of the adhesive patch or adhesive preparation of the present invention.

A schematic sectional view of the adhesive patch of another embodiment is shown in FIG. 3. In the adhesive patch of this embodiment, in at least one lateral end of the adhesive patch, thickness C of the adhesive patch at the lateral end of the adhesive layer is the same as thickness B of the central part of the adhesive patch. As a result, the effects of the present invention: (i) an adhesive patch does not easily attach to an inner wall surface of a package, and the adhesive patch can be easily taken out from the package, (ii) the release liner can be easily detached from the adhesive patch main part, (iii) the adhesive patch main part does not drop off easily from the skin, have been clarified more. Even when the adhesive patch has a peripheral part and a central part, when distance A between support upper end and release liner lower end at the lateral end of the adhesive patch is larger than thickness B of the adhesive patch central part and thickness C of the adhesive patch at the lateral end of the adhesive layer is equal to thickness B of the adhesive patch central part, the adhesive patch is encompassed in this embodiment of the adhesive patch.

Figure 4:
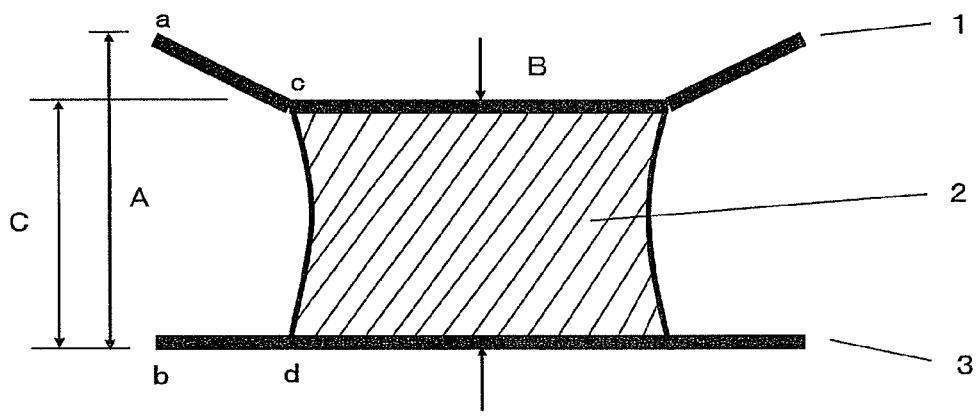
FIG. 4 is a schematic sectional view of one embodiment of the adhesive patch or adhesive preparation of the present invention.

In another preferable embodiment of the present invention, an adhesive layer end in at least one lateral end of the adhesive patch has a concave shape. To be specific, in FIG. 4 showing a schematic sectional view of the adhesive patch of the embodiment, the cross section of the lateral end of the adhesive layer 2 has a recessed circular arcuate on the central part side. With this constitution, the release liner can be easily detached from the adhesive patch. While the aforementioned constitution can be formed by various methods, for example, the side face of the adhesive layer can be processed by laser irradiation and the like.

While the support used for the adhesive patch of the present invention is not particularly limited, a support which is substantially drug impermeable, namely, a support made of a material which does not permit an active ingredient, an additive and the like in the adhesive layer to pass through the support and be lost from the back face of the adhesive patch to cause a decreased content is preferable.

In the present invention, a single film of a resin or a metal foil, or a laminate thereof is used as a support. To improve adhesiveness (anchoring property) between a support and an adhesive layer, a laminate of a porous material and a resin film is preferably used. In this case, an adhesive layer is laminated on the porous material of the laminate. Porous materials have concaves and convexes, and have voids (air bubbles) in itself. Since an adhesive layer can enter into the aforementioned voids, they can effectively suppress oozing or protruding of adhesive layer components.

Examples of the above-mentioned porous material include porous film and sheet. When the sheet has a thickness of not less than 200 µm, a porous film is preferably used. The aforementioned porous film may be a single layer film or a laminate film, and one having an anchoring property to suppress movement of the adhesive layer to the porous material can be preferably used. Specific examples include paper, woven fabric, non-woven fabric, knitted fabric, mechanically perforation-treated film and metal foil, laminates thereof and the like. Of these, paper, woven fabric, non-woven fabric, and laminates thereof are particularly preferable from the aspects of handling performance and the like, and non-woven fabric is especially preferable.

The porous material and resin film may be made of the same materials or different materials. These can be laminated according to a known method. They may contain various additives such as antioxidant, pigment, antistatic agent and the like as appropriate as long as the characteristics of the invention are not impaired. In addition, the surface thereof may be subjected to a corona discharge treatment, an ultraviolet irradiation treatment and the like.

Examples of the material of the aforementioned porous material and resin film constituting the support include polyester-based resin such as poly(ethylene terephthalate) and the like; polyamide-based resin such as nylon and the like; olefin-based resin such as polyethylene, polypropylene and the like; vinyl-based resin such as polyvinylidene chloride including Saran (registered trade mark of Asahi Kasei Corporation or Dow Chemical Company, USA), polyvinyl chloride, ionomer resin including Surlyn (registered trade mark of DuPont, USA) and the like; acrylic resin such as ethylene-ethyl acrylate copolymer and the like; fluorocarbon resin such as polytetrafluoroethylene and the like; combinations thereof and the like.

As mentioned later, when a production method characterized by pressing and heating of an area corresponding to the peripheral part of an adhesive patch is employed, porous material and resin film constituting a support are preferably made of a material that deforms by heating and softening and maintains the deformed shape after cooling, so that adhesive layer components can moderately move and a desired shape can be molded. As such material, a thermoplastic resin, for example, a polyester-based resin; an olefin-based resin such as polypropylene, polyethylene and the like are preferable, and a polyester-based resin, for example, poly(ethylene terephthalate), is particularly preferable.

The thickness of the porous material is preferably within the range of 10-100 µm so as to afford improved anchoring property, flexibility of the entire adhesive patch, attaching operability and the like. When a woven fabric or non-woven fabric is used as a porous material, the basis weight thereof is preferably 5-50 g/m$^2$, more preferably 10-30 g/m$^2$, to secure sufficient voids and achieve anchoring property.

The thickness of the above-mentioned porous material is measured by staining an adhesive patch with an aqueous ruthenium acid solution, imaging a section produced with a freezing microtome with a super high-resolution field emission scanning electron microscope (FE-SEM) at 50- to 1000-power, and reading the gauge scale. In this case, concaves and convexes are present on the surface of the porous material. In a sectional image, 10 convexes are selected at random, and an average of the thickness of the porous material at the convexes is calculated and taken as the thickness of the porous material.

In the present invention, moreover, the basis weight of the porous material is determined by multiplying the thickness of the above-mentioned porous material by the specific gravity (apparent specific gravity) of the porous material and calculating the weight of the porous material per unit area.

A resin film to be laminated on a porous material may be a single layer film or a laminate film. A nonporous film made of a resin impermeable to the active ingredient is preferable. Such resin films suppress permeation of adhesive layer components through the back face of the support to reduce the content thereof. In addition, when the adhesive layer contains a drug, they are preferably used to achieve an effect of what is called an occlusive dressing technique (ODT).

While the thickness of the resin film is not particularly limited, it is preferably 1-45 µm. When it is not less than 1 µm, the moldability becomes good, operability becomes superior, and handling is facilitated. On the other hand, when it is not more than 45 µm, an uncomfortable feeling occurs less often during application to the skin, due to the rigidity of the resin film. As mentioned later, when a production method characterized by pressing and heating of an area corresponding to the peripheral part of an adhesive patch is employed, good moldability is observed. In the present invention, the thickness of the resin film is measured in the same manner as for the above-mentioned porous material.

Thus, as a support preferably used in the present invention, a laminate film of a polyester-based film with 1-45 µm thickness (more preferably, poly(ethylene terephthalate) film) and a non-woven fabric made of polyester-based resin (more preferably, poly(ethylene terephthalate)) having a basis weight of 10-30 g/m$^2$ can be mentioned.

In consideration of the skin-following ability and comfortableness during application of an adhesive patch, the total thickness of the support is preferably 5-200 µm.

The constituent components of the adhesive layer and production method thereof are explained below. The amount of each component described in the following for the production of the adhesive layer is a ratio in wt % of the amount of each component relative to the amount of whole components except solvent.

The adhesive layer can be formed by adding an adhesive together with components such as a drug, a tackifier, an organic liquid component and the like as necessary to a solvent and mixing them to give a composition for formation of an adhesive layer, forming layers thereof by a method such as coating and the like, and drying the layers. The adhesive layer is preferably a hydrophobic adhesive layer in view of adhesion to the skin, and therefore, an anhydrous adhesive layer is preferable. From such aspect, the aforementioned solvent is preferably an organic solvent.

While the adhesive constituting the adhesive layer is not particularly limited, examples thereof include acrylic adhesives comprising acrylic polymer; styrene-diene-styrene block copolymers (e.g., styrene-isoprene-styrene block copolymer, styrene-butadiene-styrene block copolymer, etc.); rubber-based adhesives such as polyisoprene, polyisobutylene, polybutadiene and the like; silicone-based adhesives such as silicone rubber, dimethylsiloxane-based, diphenylsiloxane-based and the like; vinyl ether-based adhesives such as poly(vinyl methyl ether), poly(vinyl ethyl ether), poly(vinyl isobutyl ether) and the like; vinyl ester-based adhesives such as vinyl acetate-ethylene copolymer and the like; polyester-based adhesives comprising carboxylate component such as dimethyl terephthalate, dimethyl isophthalate, dimethyl phthalate, etc., and polyvalent alcohol components such as ethylene glycol, etc. and the like.

The adhesive layer may be a cross-linked adhesive layer obtained by subjecting the aforementioned adhesive layer to a cross-linking treatment, or a non-cross-linked adhesive layer obtained without a cross-linking treatment in the present invention. Here, the cross-linking treatment refers to a known treatment which can form bonds between molecules or in a molecule in an adhesive layer component constituting the adhesive layer. The crosslinking treatment simultaneously enables maintenance of sufficient skin adhesive force of an adhesive patch and reduction of skin irritation such as pulling feeling of the skin and physical scraping of the stratum corneum of the skin during peeling off of the adhesive patch from the skin surface. Examples of the cross-linking treatment include a chemical crosslinking treatment using a crosslinking agent, a treatment for ion cross-linking, and a physical crosslinking treatment using electron beam, ultraviolet light and the like. Examples of the crosslinking agent include metal salts such as zinc acetate and the like, an epoxy compound, an amide compound, an amine compound, acid anhydride, peroxide, an isocyanate compound and the like.

When the adhesive layer is a non-cross-linked adhesive layer, adhesive layer components tend to ooze or protrude from the end of the adhesive patch. Even when the adhesive layer is a non-cross-linked adhesive layer, the adhesive patch of the present invention can effectively suppress oozing or protruding of the adhesive layer components, and is particularly advantageous in such case.

Similarly, when the adhesive layer comprises a rubber-based adhesive, adhesive layer components tend to ooze or protrude from the end of the adhesive patch, and the adhesive patch of the present invention is particularly advantageous in such case.

To achieve appropriate adhesive force and dissolution property of drugs, a mixture of the same component or different components having different average molecular weights can be used as a rubber-based adhesive. To explain with polyisobutylene as an example, a mixture of high molecular weight polyisobutylene having a viscosity average molecular weight of 1,800,000-5,500,000, medium molecular weight polyisobutylene having a viscosity average molecular weight of 40,000-85,000 and, where necessary, lower molecular weight polyisobutylene is preferable. The viscosity average molecular weight in the present invention is calculated by measuring flow time at 20° C. using Ubbelohde viscometer with capillary 1, calculating a Staudinger index ($J_0$) according to the following Schulz-Blaschke equation (equation (1)), and then assigning the aforementioned $J_0$ value to the following Mark Houwink-Sakurada equation (equation (2)).

$$J_0 = \eta_{sp}/c(1+A\eta_{sp}) \quad (1)$$

wherein, $\eta_{sp} = t/t_0 - 1$ t; flow time of solution (by Hagenbach-couette correction equation)

$t_0$; flow time of solvent (by Hagenbach-couette correction equation)

c; concentration of solution (g/cm$^3$)

A; specific constant of polymer solution $$J_0 = kM_v^\alpha \quad (2)$$

Mv; viscosity average molecular weight k, α; specific constant of polymer

In the case of polyisobutylene, A=0.31, k=3.06×10$^{-2}$, α=0.65 are inserted into the above-mentioned equation (1) and equation (2), and Mv value can be calculated from $J_0$ value.

When polyisobutylene is used as an adhesive, a high molecular weight polyisobutylene is generally added at 10 wt %-80 wt %, preferably 10 wt %-50 wt %, a medium molecular weight polyisobutylene is generally added at 0 wt %-90 wt %, preferably 10 wt %-80 wt %, and a low molecular weight polyisobutylene is generally added at 0 wt %-80 wt %, preferably 0 wt %-60 wt %. A generally used adhesive layer becomes stiff when the proportion of a high molecular weight component increases, and soft when the proportion of a low molecular weight component increases.

To confer an adequate adhesiveness to the adhesive layer, for example, a tackifier such as rosin-based resin, polyterpene resin, chroman-indene resin, petroleum-based resin, terpene-phenol resin, xylene resin and the like may be contained. These may be used alone or in a mixture of two or more kinds thereof. Examples of the aforementioned petroleum-based resin include aliphatic (C5-based) petroleum resin, aromatic (C9-based) petroleum resin, copolymer series (C5-C9-based) petroleum resin and alicyclic saturated hydrocarbon resin obtained by partially or completely hydrogenating aromatic (C9-based) petroleum resin. As the alicyclic saturated hydrocarbon resin, one having a softening point by ring and ball method of 90-150° C. is preferable. While the amount of the tackifier is not particularly limited, it is, for example, 10 wt %-40 wt % from the aspects of imparting of appropriate adhesiveness and cost-effectiveness.

When desired, the adhesive layer can contain an organic liquid component. An organic liquid component is not particularly limited as long as it is liquid at room temperature (25° C.), or is a mixture of two or more kinds which finally becomes liquid at room temperature (25° C.). Examples of the organic liquid component include glycols such as ethylene glycol, propylene glycol, butylene glycol, diethylene glycol, dipropylene glycol, triethylene glycol, tripropylene glycol, poly(ethylene glycol), poly(propylene glycol) and the like; vegetable fats and oils such as olive oil, castor oil and the like; animal fats and oils such as liquid lanolin; hydrocarbons such as squalane and liquid paraffin; various surfactants; ethoxylated stearyl alcohol; glycerol monoesters of fatty acids such as oleic acid monoglyceride, caprylic acid monoglyceride and lauryl acid monoglyceride; dialkyl esters of polyalkylene glycol such as polyethylene glycol dilaurate, polyethylene glycol diisostearate, polypropylene glycol diisostearate, polypropylene glycol dioleate and the like; glycerol diesters such as glycerol diacetate and the like; glycerol triesters such as glyceroltriacetate and the like, or a mixture thereof; alkylesters of fatty acid such as triethyl citrate and the like; long chain alcohols such as isostearyl alcohol, oleyl alcohol and the like; higher fatty acids such as caprylic acid, oleic acid, linoleic acid; alkylesters of higher fatty acid such as isopropyl myristate; pyrrolidones such as N-methylpyrrolidone, N-dodecylpyrrolidone; sulfoxides such as decylmethylsulfoxide; and the like. These can be used alone or in a mixture of two or more kinds thereof.

The content of the above-mentioned organic liquid component is preferably 10 wt %-60 wt, more preferably 15 wt %-60 wt %, most preferably 20 wt %-60 wt %. When the content of the component is not less than 10 wt %, the adhesive layer is easily plasticized, and adhesive layer components easily ooze or protrude from the end of the adhesive layer. Therefore, the present invention capable of effectively suppressing such phenomenon is advantageous in such cases. When an organic liquid component is contained in a proportion of more than 60 wt %, an adhesive layer may not be able to maintain a given shape.

While the organic solvent to be used for the production of an adhesive layer in the present invention is not particularly limited, one compatible with the above-mentioned components constituting the adhesive layer and permitting easy volatilization in a drying step is preferable. Examples of the organic liquid solvent include aromatic hydrocarbons such as benzene, toluene, xylene and the like; aliphatic hydrocarbon such as, n-hexane and the like; esters such as ethyl acetate and the like; alcohols such as methanol, ethanol, isopropanol and the like; ethers such as diethyl ether, tetrahydrofuran and the like; ketones such as acetone and the like; and the like. These may be used alone or in a mixture of two or more kinds thereof.

While the method of mixing the aforementioned respective components is not limited, examples thereof include kneading machines such as kneader, planetary mixer, Henschel mixer, roll mill; dispersing machines such as colloid mill, homogenizer and the like; stirring machines such as propeller-type blade stirring machine and the like; and the like. These can be used alone or in a combination of two or more kinds thereof.

A composition to form an adhesive layer can be applied with, for example, a conventionally-used coater such as a rotogravure roll coater, a reverse roll coater, a kiss-roll coater, a dip roll coater, a bar coater, a knife coater, a spray coater and the like. For promotion of crosslinking reaction, improvement of production efficiency and the like, the aforementioned composition is preferably dried under heating. Depending on the kind of the support to be coated with the composition, the drying temperature is, for example, about 40° C.-150° C.

The aforementioned drying may be performed by air-drying, or according to a known method using a dryer, hot air, far-infrared radiation and the like.

In the adhesive patch of the present invention, an adhesive layer has a thickness of 50 μm-500 μm, more preferably 100 μm-300 μm, in the core part of the adhesive patch. Moreover, the thickness of the adhesive layer in the entire central part of the adhesive patch is preferably within the aforementioned range. When an adhesive layer has a thickness within the aforementioned range, it is superior in the skin protection effect, can sufficiently contain an active ingredient such as a drug and the like, and is superior in the skin adhesion performance.

A release liner to protect the adhesive surface can be laminated on the adhesive surface of the adhesive layer of the adhesive patch main part, before applying the adhesive patch main part to the skin. The release liner is not particularly limited, and examples of the material thereof include those known per se in the field. Specific examples thereof include plastic films of polyester-based resin film such as poly(ethylene terephthalate); vinyl-based resin film such as poly(vinyl chloride), poly(vinylidene chloride), polystyrene and the like; acrylic resin film such as various acrylic and methacrylic polymers; polycarbonate resin film; polyimide resin film; cellulose-based resin film such as acetyl cellulose, regenerated cellulose (cellophane), celluloid and the like; a laminate film of high-quality paper, glassine paper and the like and polyolefin-based film and the like. For safety, economic efficiency and drug-transfer properties, a polyester-based resin film is preferably used. The thickness of the aforementioned release liner is generally 10 μm-200 μm, preferably 25 μm-100 μm.

The release liner is preferably treated for easy peeling on the interfacial surface side with an adhesive layer, so as to facilitate peeling from the adhesive layer. While the easy peeling treatment is not particularly limited, a known method can be applied. For example, a treatment method for forming a peeling-treated layer using a release agent containing a curable silicone resin as a main component by a coating method such as bar coating, gravure coating and the like can be mentioned.

The thickness of the aforementioned peeling-treated layer is preferably 0.01 μm-5 μm to ensure releaseability and uniformity of the coating. The thickness of the release liner having a peeling-treated layer is generally 10 μm-200 μm, preferably 50 μm-100 μm, from the aspect of handling property.

The release liner in the adhesive patch of the present invention may have an extended part outwardly extending over the adhesive patch main part. Since the extended part decreases the frequency of contact of the end of the adhesive patch main part against the inside of the package when the adhesive patch is contained in the package, even when an adhesive layer component oozes or protrudes from the end of the adhesive patch main part, adhesion thereof to the inside of package which causes difficulty in taking the adhesive patch out from the package can be suppressed. To provide such effects, at least one part of the peripheral part of the adhesive patch main part preferably has a release liner with an extended part, and more preferably, the whole peripheral part of the adhesive patch main part has a release liner with an extended part. The length of the aforementioned extended part of the release liner is preferably about 0.5 mm-10 mm, more preferably about 1 mm-3 mm, so as to achieve the aforementioned effects and ensure smooth insertion into a package.

The release liner may also have a back split part. The aforementioned back split part is made by forming a broken line on the surface on the opposite side from the contact surface of the release liner with the adhesive layer. The shape of the aforementioned broken line may be linear or curve (e.g., wave shape), or a combination of these. The broken line may be a solid line or a dashed line, or a combination of these. Since a release liner has a back split part, the release liner can be easily removed when the adhesive patch is used.

In the present invention, an adhesive layer may contain a drug when desired to form an adhesive preparation. The drug here is not particularly limited, and any of drugs for systemic action and drugs for local action can be used. A drug that can be administered to a mammal such as human and the like through the skin, that is, a transdermal absorptive drug is preferable. Such drugs specifically include, for example, general anesthetics, antipsychotic agents, antidepressants, mood stabilizers, psychostimulants, hypnotics, antianxiety drugs, antiepileptic drugs, therapeutic drugs for migraine, antiemetic drugs, drugs for dizziness, local anesthetics, muscle relaxants, autonomic drugs, antispastic drugs, therapeutic drugs for Parkinson's disease, corticosteroids, nonsteroidal antiinflammatory drugs, analgesic-antipyretics, antirheumatic drugs, anti-histamine drugs, antiallergic agents, cardiac stimulants, antiarrhythmic drugs, diuretics, depressors, vasoconstrictors, vasodilators, therapeutic drugs for angina pectoris, anapnoics, bronchodilators, therapeutic drugs for bronchial asthma, antitussives, expectorants, hormone drugs, hematinics, hemostatic drugs, antithrombotic drugs, therapeutic drugs for gout•hyperuricemia, therapeutic drugs for diabetes, therapeutic drugs for hyperlipidemia, antineoplastic drugs, immunosuppressive drugs, antibacterial agents, chemical therapy drugs, antifungal agents, antiviral drugs, antiparasitic drugs, narcotics, stop smoking aids and the like. These drugs may be used in a free form or a salt form.

The content of the above-mentioned drug in the adhesive preparation is not particularly limited as long as the effect of the drug for transdermal absorption can be sufficiently exerted, and the adhesion property and the like of an adhesive layer are not impaired. It is preferably 0.1 wt %-60 wt %, more preferably 0.5 wt %-40 wt %, of the adhesive layer. When it is lower than 0.1 wt %, a sufficient treatment effect may not be obtained, and when it is higher than 60 wt %, skin irritation may occur, as well as a treatment effect may not be improved, thus providing economical disadvantages.

As the production method of the adhesive patch, various methods are available as mentioned in the above explanation of the shape and the like of the adhesive patch. However, for industrial production, for example, the following method is preferable for high production efficiency.

First, a composition for formation of an adhesive layer is applied to one surface of a release liner and dried to give an adhesive layer. A support is laminated thereon to give an original sheet for punching out of adhesive patch. Alternatively, a composition for formation of an adhesive layer is applied to one surface of a support and dried to give an adhesive layer. A support is laminated thereon to give an original sheet for punching out of adhesive patch. A method of the above-mentioned lamination is not particularly limited and, for example, a known method such as application of primer and the like, adhesion, fusion bonding, melt-bonding, pressure bonding and the like can be mentioned.

Then, an original sheet for punching out of adhesive patch is stamped from the support side by pressing with a heated stamp having a predetermined shape. After stamping, the aforementioned original sheet is punched out at a predetermined punching position to give the adhesive patch of the present invention. The predetermined shape of the aforementioned stamp is such a shape as presses at least an area corresponding to the peripheral part of the adhesive patch during pressing. By pressing an area corresponding to the peripheral part, an adhesive layer in the peripheral part of the adhesive patch can be decreased or removed. In addition, an adhesive patch wherein distance A between support upper end and release liner lower end at the lateral end of the adhesive patch is greater than thickness B of the central part of the adhesive patch can be efficiently obtained by pressing the aforementioned original sheet with a stamp and removing the stamp, since the support has a restoring force.

Figure 5:
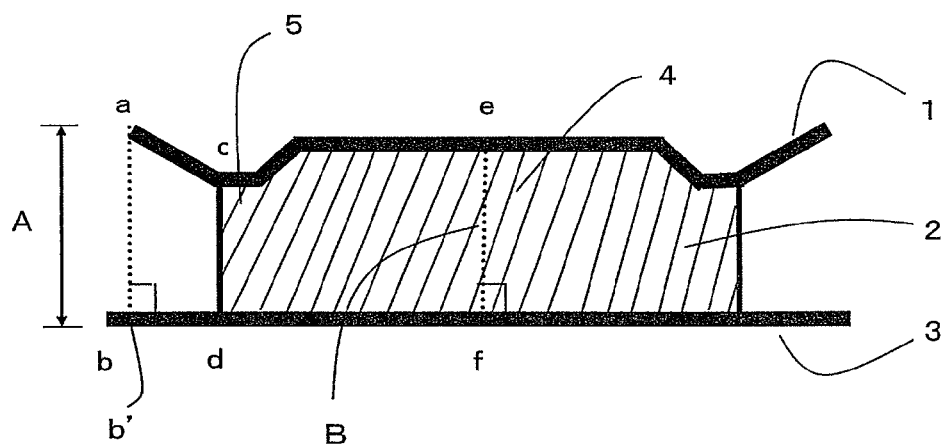
FIG. 5 is a schematic sectional view of one embodiment of the adhesive patch or adhesive preparation of the present invention.
Figure 6:
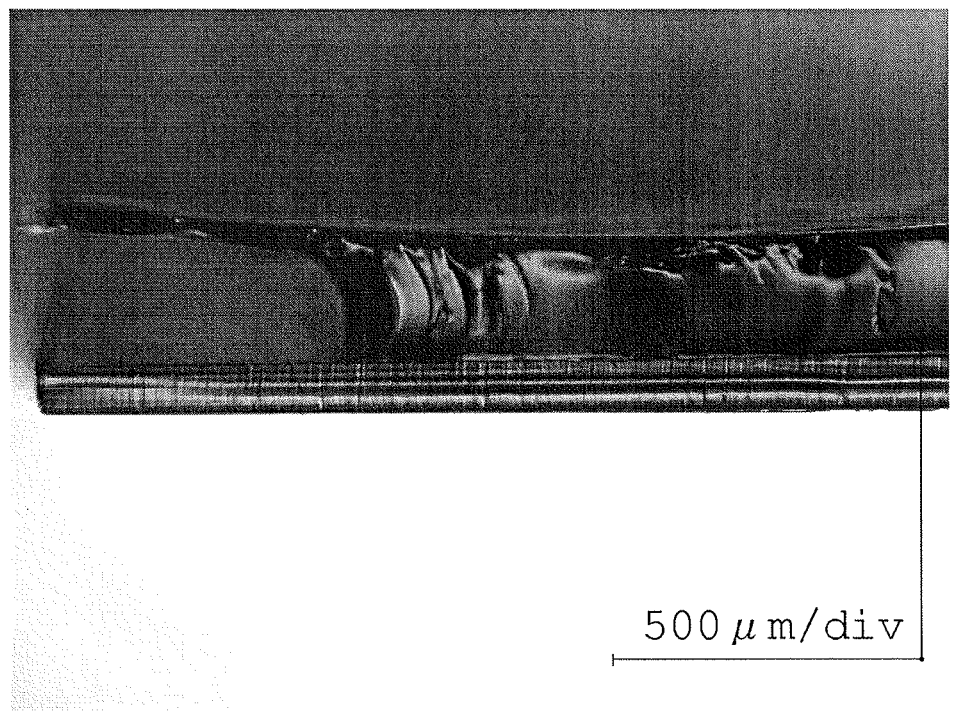
FIG. 6 is a cross sectional scanning electron micrograph of the end of the adhesive patch of Example 1.
Figure 7:
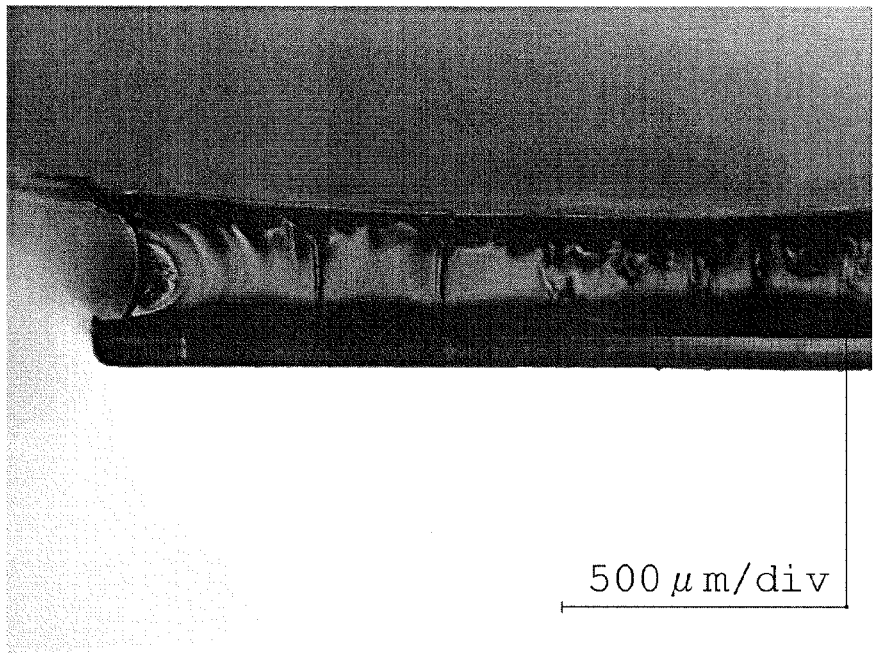
FIG. 7 is a cross sectional scanning electron micrograph of the end of the adhesive patch of Example 2.
Figure 8:
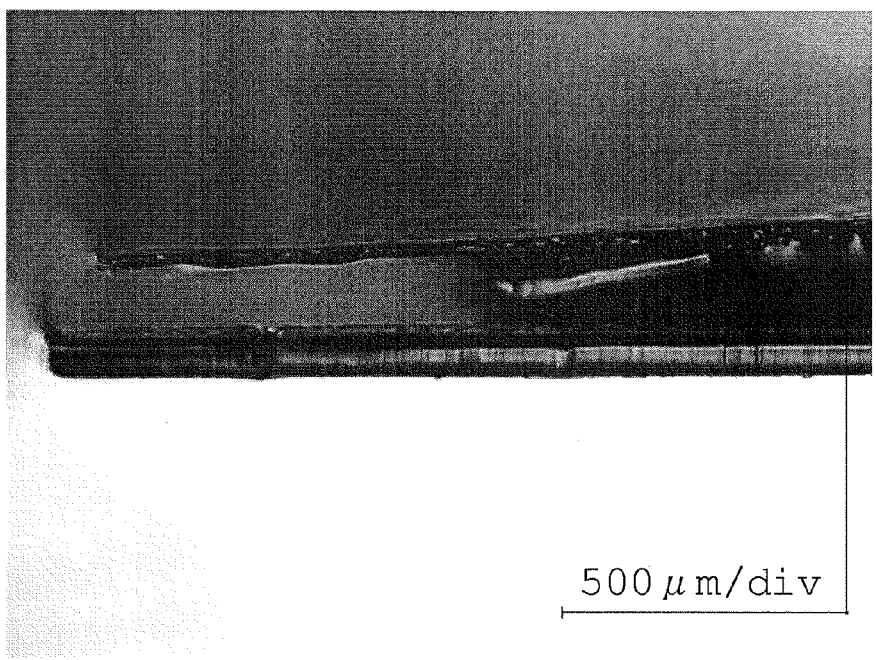
FIG. 8 is a cross sectional scanning electron micrograph of the end of the adhesive patch of Comparative Example 1.
Figure 9:
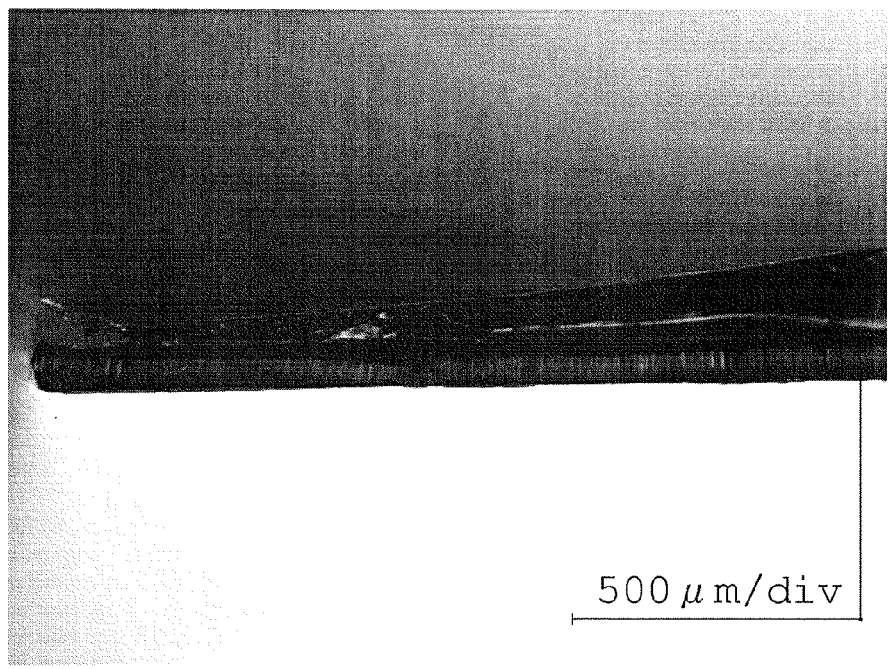
FIG. 9 is a cross sectional scanning electron micrograph of the end of the adhesive patch of Comparative Example 2.
Figure 10:
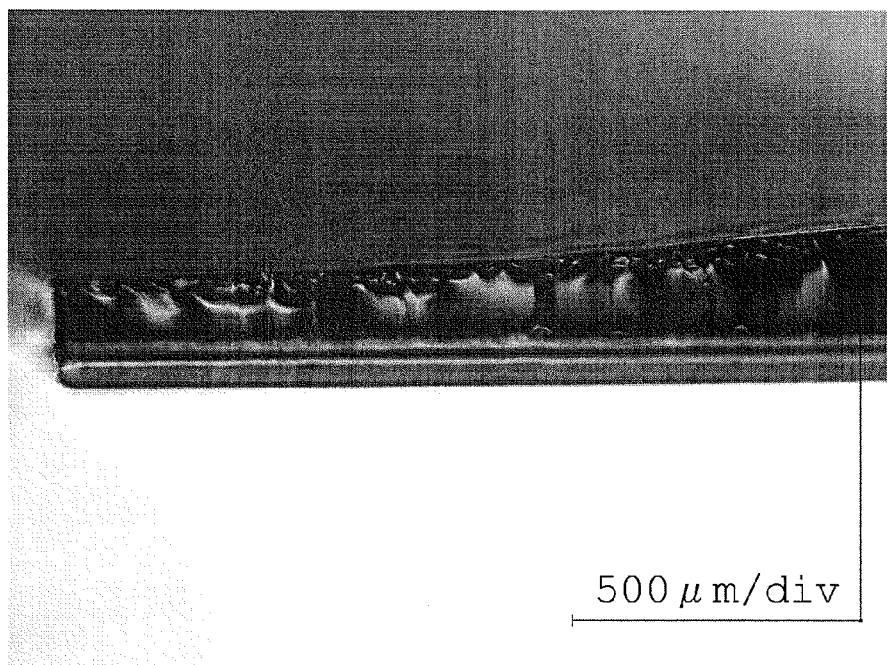
FIG. 10 is a cross sectional scanning electron micrograph of the end of the adhesive patch of Comparative Example 3.

As mentioned above, an adhesive patch wherein distance A between support upper end and release liner lower end at the lateral end is greater than thickness B of the central part of the adhesive patch can be preferably obtained by using a heated stamp. A schematic sectional view of an adhesive patch obtained by the aforementioned method is shown in FIG. 5. By stamping with a heated stamp, a support containing a part adjacent to the adhesive patch central part side of the pressed area is softened with heat. As a result, the adhesive layer in the pressed area is released, and formation of a thin peripheral part 5 having a smaller thickness than the central part 4 is encouraged. The aforementioned shape of the once-formed adhesive patch is later allowed to cool or cooled otherwise and maintains its shape. Thus, a preferable embodiment of the present invention contains, as shown in FIG. 5, a central part and a peripheral part 5 having a smaller thickness than the central part 4. While the temperature of the heated stamp varies depending on the material and thickness of a support, composition of an adhesive layer and the like, it is preferably 90° C.-200° C., more preferably 120° C.-180° C.

To form a concave lateral end of the adhesive layer and remove adhesive layer of the peripheral part, the pressure during pressing and pressing time are preferably controlled. The pressure during pressing varies depending on the material and thickness of a support, composition of an adhesive layer and the like. It is preferably $10N/10\,cm^2$-$1,000,000N/10\,cm^2$ ($1.0\times10^4 N/m^2$-$1.0\times10^9 N/m^2$), more preferably $500N/10\,cm^2$-$10,000N/10\,cm^2$ ($5.0\times10^5 N/m^2$-$1.0\times10^7 N/m^2$). The pressing time also varies depending on the material and thickness of a support, composition of an adhesive layer and the like. It is preferably 0.05 second-5 seconds, more preferably 0.1 second-2 seconds.

During stamping, the gap between the stamp and the stamping table is preferably the total thickness of a support, the peripheral part of an adhesive layer and a release liner ±10 μm.

The preferable shape of a stamp is any containing a planar section as a pressing surface that contacts and presses an adhesive patch, and is not particularly limited as long as it can specifically press only a peripheral part of the adhesive patch. The planar section as a pressing surface has a shape corresponding to the peripheral part of the adhesive patch. For example, the shape of the stamp consists of a surrounding first rectangle (square, oblong figure) on the coax and a smaller second rectangle similar thereto, and the corresponding sides of the first and second rectangles are disposed in parallel to each other. While the material of the stamp is not particularly limited, iron is preferable. Stainless steel may develop heat distortion and the processing thereof may be difficult. Aluminum and brass can be processed easily, but may be unpreferably inferior in the duration of the stamp.

The punching means for an adhesive patch and the like is not particularly limited, and a punching-out method using a laser, a press-cutting blade and the like can be mentioned. Since adjustment of cutting size and position adjustment are easy and a clear end surface can be obtained, an original sheet is preferably punched out with a press-cutting blade dies set (male type and female type).

In a preferable embodiment of the adhesive patch of the present invention, the release liner has an extended part in at least one part of the peripheral part of the adhesive patch main part and, in a more preferable embodiment, the release liner has an extended part in the whole peripheral part of the adhesive patch main part. An extended part of such at least one part of the peripheral part can be easily formed by punching out only the adhesive patch main part using a press-cutting blade dies set (male type and female type) having a required shape and then punching out the release liner.

The length of the extended release liner can be adjusted by changing the size difference in the press-cutting blade dies set male type and female type. The length of the extended release liner can be extended by increasing the size difference. When a back split part is set on a release liner, the central part of a release liner is half-cut with a die roll, and a broken line is formed only in the release liner.

The adhesive patch and adhesive preparation of the present invention are preferably preserved in a package. Such package can be produced using a packaging material generally used for packaging of adhesive patches. Examples of the packaging material include polyolefin-based resin film such as polyethylene film, polypropylene film, polymethylpentene film and the like; vinyl-based resin film such as polyvinyl chloride film, polyvinylidene chloride film, polyvinyl alcohol film, polystyrene film, polyacrylonitrile film, ionomer film and the like; polyester-based resin film such as poly(ethylene terephthalate) film and the like; polyimide-based resin film such as nylon film and the like; cellulose-based resin film such as cellophane and the like; polycarbonate resin film; and laminate film thereof; laminate film thereof and aluminum and the like. An adhesive patch can be housed in a package produced using the aforementioned packaging materials, and tightly sealed by a known method such as heat sealing and the like.

EXAMPLES

The present invention is explained in more detail in the following by referring to Examples and Comparative Examples, which are not to be construed as limitative.

Examples 1, 2 and Comparative Examples 1-3

Adhesive Preparations (1) Production of Adhesive Sheet
<Production of a Composition for Formation of an Adhesive Layer>

High molecular weight polyisobutylene (viscosity average molecular weight; 4,000,000, 0.620 kg), alicyclic saturated hydrocarbon resin (softening point by ring and ball method; 120° C.-160° C., 1.127 kg), toluene (4.456 kg) and n-hexane (4.726 kg) were weighed, and stirred in a blending tank for not less than 24 hr. Medium molecular weight polyisobutylene (viscosity average molecular weight; 55,000, 1.071 kg) was weighed, cast into the blending tank and the mixture was stirred for not less than 24 hr. Thereafter, isopropyl myristate (1.232 kg) and toluene (0.270 kg) were weighed, cast into the blending tank and the mixture was stirred for not less than 4 hr to give a composition for forming an adhesive layer.
<Production of Original Sheet for Punching Out>

The above-mentioned composition was applied to an easy-release treated surface of a release liner (thickness 75 μm) made from poly(ethylene terephthalate) (hereinafter to be indicated as "PET") with a coater consisting of a back roll and a comma roll, such that the thickness of the adhesive layer after drying was 160 μm, and dried. The obtained adhesive surface of the adhesive layer was adhered to a PET non-woven fabric surface of a support, which is a laminate of a 3.5 μm-thick PET film and a PET non-woven fabric (basis weight: 10 g/m$^2$-20 g/m$^2$), by pressure bonding to give an original sheet for punching out of adhesive patch.

(2) Formation of Adhesive Patch by Punching and Packaging Machine

The above-mentioned original sheet for adhesive patch punching out was punched out by a punching and packaging machine equipped with a stamping part (hot-pressing+stamping metal mold) and a die set metal mold (male type, female type) to give an adhesive patch. The stamping width of the stamping part, heating temperature and pressure during stamping were adjusted as shown in Table 1 to give the adhesive patches of Examples 1 and 2, and Comparative Examples 1-3.

TABLE 1

| sample | stamping width (mm) | heating temperature of stamp (° C.) | pressure during stamping (N/10 cm$^2$) | pressing time (second) |
|---|---|---|---|---|
| Example 1 | 3 | 150 | 10,000 | 0.25 |
| Example 2 | 3 | 150 | 10,000 | 0.10 |
| Comparative Example 1 | 3 | >200 | 10,000 | 0.25 |
| Comparative Example 2 | 3 | >200 | 10,000 | 5.00 |
| Comparative Example 3 | 3 | <90 | 10,000 | 0.05 |

Experimental Example 1

Evaluation of Adhesive Patch Shape

Each adhesive patch of Example and Comparative Example was stained with an aqueous ruthenium acid solution, and cut with a frozen microtome (LR-85 manufactured by YAMATO KOHKI INDUSTRIAL CO., LTD.). The section was taken by FE-SEM (S-4800 manufactured by Hitachi, Ltd.) at 50-power to 1000-power. In the electron micrograph of each adhesive patch, the gauge scales of the peripheral part and the central part were read, whereby the thicknesses of the PET film and the PET non-woven fabric, and the thickness (total of thickness of adhesive layer and thickness of support) of the adhesive patch main part were measured. In this case, concaves and convexes are present on the surface of the PET non-woven fabric. In a sectional image, 10 convexes are selected at random, and an average of the thickness of the PET non-woven fabric at the convexes was calculated and taken as the thickness of the PET non-woven fabric. Then, the thickness of the PET film and the thickness of the aforementioned PET non-woven fabric were subtracted from the thickness of the adhesive patch main part, and the thicknesses of the adhesive layer at the peripheral part and the central part were determined. In addition, distance A between the upper end of the support and the lower end of the release liner at the lateral end of the adhesive patch, and the distance between the lateral end of the adhesive layer on the central part side, from the lateral end of the support was measured. Sectional images of the end of respective adhesive patches of the Examples and Comparative Examples are shown in FIG. 6-FIG. 10.

From the sectional images of the end of respective adhesive patches of the Examples and Comparative Examples, the respective adhesive patches of Examples and Comparative Examples were observed for (1) whether, in a lateral end, the lateral end of the adhesive layer is located toward the central part side of the adhesive patch from the lateral end of the support, (2) whether the distance between the upper end of the support and the lower end of the release liner at the lateral end is greater than the thickness of the central part of the adhesive patch, and (3) whether the end of the adhesive layer has a concave shape. When the observation result is a 'yes', Y is marked and when the result is a 'no', N is marked in Table 2. In each adhesive patch, the thickness of the central part of the adhesive layer was the same as that of the adhesive layer after drying the original sheet for punching out, and was 160 μm. In the adhesive patches of Examples 1 and 2, moreover, distance A between the upper end of the support and the lower end of the release liner at the lateral end was within the range of 101%-150% of the thickness of the central part of the adhesive patch. In the adhesive patch of Example 1, the lateral end of the adhesive layer was located at 500 μm toward the central part side of the adhesive patch from the lateral end of the support. On the other hand, in the adhesive patch of Example 2, the lateral end of the adhesive layer was located at 50 μm toward the central part side of the adhesive patch from the lateral end of the support.

Experimental Example 2

Evaluation of Performance of Taking-Out of Adhesive Patch from Package

Figure 11:
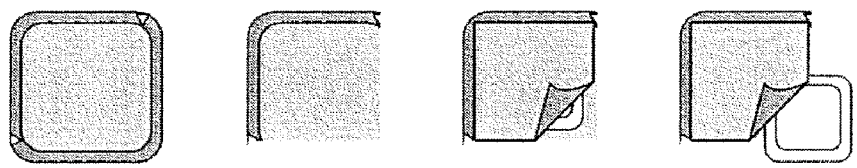
FIG. 11 shows that an adhesive patch package is opened by cutting two sides with scissors or along a V-shaped notch, and the adhesive patch is taken out.

As shown in FIG. 11, two sides of the adhesive patch package were opened with scissors or along V-shaped notches. The adhesive patch was taken out while holding a corner thereof, and the performance of taking-out of the adhesive patch from the package was evaluated according to the following three-step evaluation criteria.
<Evaluation Criteria>
○; no oozing or protruding of adhesive layer components; easy taking out was possible
Δ; oozing or protruding of adhesive layer components in a part of adhesive patch; taking out was possible
x; remarkable oozing or protruding of adhesive layer components; taking out was difficult Experimental Example 3

Evaluation of Skin Adhesion Performance

A specialized estimator took out an adhesive patch from a package, adhered the patch to the chest for 24 hr from the morning, and evaluated the adhesion state according to the following three-step evaluation criteria. During adhesion of the adhesive patch, the estimator behaved as usual. When the estimator took a bath in the morning, the patch was adhered avoiding immediately after taking a bath (within 30 min). The same one estimator evaluated each adhesive patch of Example and Comparative Example once.
<Evaluation Criteria>
○; adhesive patch did not drop off for 24 hr; end of adhesive patch did not turn up
Δ; adhesive patch did not drop off for 24 hr; end of adhesive patch turned up
x; adhesive patch dropped off within 24 hr Experimental Example 4

Evaluation of Releaseability of a Release Liner

Five male panelists (50 years of age or above) detached a release liner from an adhesive patch, and evaluated the releaseability thereof by sensory evaluation. The evaluation results were summarized by the following criteria.
<Summary Criteria of Evaluation>
○; all panelists felt easy detachability
Δ; part of panelists felt difficulty in detachment
x; all panelists felt difficulty in detachment
The evaluation results of the above-mentioned Experimental Examples 2-4 are also shown in Table 2.

TABLE 2

| | shape of lateral end of adhesive patch | | | evaluation results | | |
|---|---|---|---|---|---|---|
| sample | lateral end of adhesive layer is located toward central part side of adhesive patch from lateral end of support | distance between upper end of support and lower end of release liner at lateral end is greater than thickness of central part | concave end of adhesive layer at lateral end | performance in taking out from package | skin adhesion performance | releaseability of release liner |
| Example 1 | Y | Y | Y | ○ | ○ | ○ |
| Example 2 | Y | Y | Y | ○ | ○ | Δ |
| Comparative Example 1 | Y | N | Y | ○ | x | Δ |
| Comparative Example 2 | Y | N | N | ○ | x | x |
| Comparative Example 3 | N | N | N | x | x | x |

From Table 2, it is clear that, in the adhesive patches of Examples 1 and 2 of the present invention, the lateral end of the adhesive layer was located toward the central part side of the adhesive patch from the lateral end of the support, at the lateral end; the distance between the upper end of the support and the lower end of the release liner at the lateral end was greater than the thickness of the central part of the adhesive patch; and the end of the adhesive layer was concave in the lateral end. These adhesive patches received good evaluation results as to the taking out performance from a package and skin adhesion performance. The adhesive patch of Example 1 wherein the lateral end of the adhesive layer is located at 500 μm on the central part side of the adhesive patch from the lateral end of the support received still higher evaluation with regard to the releaseability of the release liner, as compared to the adhesive patch of Example 2 wherein the lateral end of the adhesive layer is located at 50 μm on the central part side of the adhesive patch from the lateral end of the support. In contrast, the adhesive patch of Comparative Example 1 wherein the distance between the upper end of the support and the lower end of the release liner at the lateral end is not greater than the thickness of the central part of the adhesive patch received lower evaluation with regard to the skin adhesion performance. Furthermore, the adhesive patch of Comparative Example 2 wherein the end of the adhesive layer is not concave in the lateral end received lower evaluation also with regard to the releaseability of the release liner. The adhesive patch of Comparative Example 3 wherein the lateral end of the adhesive layer is not located toward the central part side of the adhesive patch from the lateral end of the support, at the lateral end; the distance between the upper end of the support and the lower end of the release liner at the lateral end is not greater than the thickness of the central part of the adhesive patch; and the end of the adhesive layer is not concave in the lateral end did not receive good evaluation with regard to the taking-out performance from a package, skin adhesion performance and releaseability of a release liner.

Examples 3 and 4

Patch Preparation

To the above-mentioned composition for formation of an adhesive layer was added 1 part by weight of indomethacin (anti-inflammatory agent) per 100 parts by weight of the whole blended components except toluene, whereby a composition for formation of an adhesive layer for a transdermal absorptive preparation was prepared. Using the aforementioned composition and in the same manner as in the above-mentioned Examples 1 and 2, adhesive preparations were obtained. The adhesive preparations of Examples 3 and 4 afford effects similar to those of the adhesive patches of the above-mentioned Examples 1 and 2 in the taking-out performance from a package, skin adhesion performance and releaseability of a release liner.

INDUSTRIAL APPLICABILITY

As described in detail in the above, the present invention can provide an adhesive patch or adhesive preparation, which is free of oozing and protruding of an adhesive layer component from an end, suppresses occurrence of so-called cold flow phenomenon during preservation, does not easily attach to the inner surface of a package, can be taken out with ease from a package, and less often causes an unpleasant feeling due to stickiness to the hand and sticky feeling on the application site during use. In addition, the present invention can provide an adhesive patch or adhesive preparation which ensures sufficient skin adhesion, is highly resistant to the detachment from the skin surface, and permits easy detachment of the release liner, wherein the frequency of rubbing of the end against clothes etc. is reduced during adhesion to the skin, and the end is not turned up easily.

EXPLANATION OF SYMBOLS 1 support
2 adhesive layer
3 release liner
4 central part
5 peripheral part
a upper end of support at lateral end of adhesive patch
b lower end of release liner at lateral end of adhesive patch
b' intersection point of perpendicular line drawn from upper end a of support at lateral end of adhesive patch to lower end of release liner, and lower end of release liner
c upper end of support at lateral end of adhesive layer
d lower end of release liner at lateral end of adhesive layer
d' intersection point of perpendicular line drawn from upper end c of support at lateral end of adhesive layer to lower end of release liner, and lower end of release liner
e upper end of support at core part of adhesive patch
f intersection point of perpendicular line drawn from upper end e of support at core part of adhesive patch to lower end of release liner, and lower end of release liner
A distance between upper end of support and lower end of release liner at lateral end of adhesive patch
B thickness of central part of adhesive patch
C thickness of adhesive patch at lateral end of adhesive layer

The invention claimed is:

1. An adhesive patch comprising a support, an adhesive layer on at least one surface of the support, and a release liner on a surface of the adhesive layer opposite from the support, wherein
  (a) the lateral end of the adhesive layer is exposed,
  (b) in at least one lateral end, the lateral end of the adhesive layer is located toward the central part side of the adhesive patch from the lateral end of the support, and
  (c) when placed horizontally with the release liner facing down, a distance A between the upper end of the support and the lower end of the release liner at said lateral end of the adhesive patch is greater than a thickness B of the central part of the adhesive patch.

2. The adhesive patch according to claim 1, wherein, in at least one lateral end, the lateral end of the adhesive layer is located on the central part side of the adhesive patch at 1 μm-1000 μm from the lateral end of the support.

3. The adhesive patch according to claim 1, wherein, in at least one lateral end, the distance A between the upper end of the support and the lower end of the release liner at said lateral end of the adhesive patch is greater than a thickness C of the adhesive patch at the lateral end of the adhesive layer.

4. The adhesive patch according to claim 1, wherein, in at least one lateral end, the thickness C of the adhesive patch at the lateral end of the adhesive layer is equal to the thickness B of the central part of the adhesive patch.

5. The adhesive patch according to claim 1, wherein, in at least one lateral end, the end of the adhesive layer has a concave shape.

6. The adhesive patch according to claim 1, wherein the adhesive layer comprises a rubber-based adhesive.

7. The adhesive patch according to claim 1, wherein the adhesive layer is not crosslinked.

8. The adhesive patch according to claim 1, wherein the adhesive layer comprises an organic liquid component.

9. An adhesive preparation comprising the adhesive patch according to claim 1, wherein the adhesive layer contains a drug.

10. An adhesive preparation comprising the adhesive patch according to claim 2, wherein the adhesive layer contains a drug.

11. An adhesive preparation comprising the adhesive patch according to claim 3, wherein the adhesive layer contains a drug.

12. An adhesive preparation comprising the adhesive patch according to claim 4, wherein the adhesive layer contains a drug.

13. An adhesive preparation comprising the adhesive patch according to claim 5, wherein the adhesive layer contains a drug.

14. An adhesive preparation comprising the adhesive patch according to claim 6, wherein the adhesive layer contains a drug.

15. An adhesive preparation comprising the adhesive patch according to claim 7, wherein the adhesive layer contains a drug.

16. An adhesive preparation comprising the adhesive patch according to claim 8, wherein the adhesive layer contains a drug.

* * * * *